United States Patent
Ashmead et al.

(10) Patent No.: US 6,407,138 B1
(45) Date of Patent: Jun. 18, 2002

(54) COMPOSITION AND METHOD FOR PREPARING ELECTRICALLY NEUTRAL AMINO ACID CHELATES FREE OF INTERFERING IONS

(75) Inventors: Stephen D. Ashmead, Clinton; David C. Wheelwright, Layton; Clayton Ericson, Morgan; Mark Pedersen, Kaysville, all of UT (US)

(73) Assignee: Albion International, Inc., Clearfield, UT (US)

( * ) Notice: Subject to any disclaimer, the term of this patent is extended or adjusted under 35 U.S.C. 154(b) by 0 days.

(21) Appl. No.: 09/686,684

(22) Filed: Oct. 11, 2000

(51) Int. Cl.$^7$ ............................................... A61K 31/28
(52) U.S. Cl. ...................... 514/492; 562/553; 514/494; 514/499; 514/501; 514/502; 514/561; 556/50
(58) Field of Search ........................... 556/50; 562/553; 514/492, 494, 499, 501, 502, 561, 574

(56) References Cited

U.S. PATENT DOCUMENTS

| | | |
|---|---|---|
| 2,396,115 A | 3/1946 | Nicholls |
| 3,440,054 A | 4/1969 | Sair |
| 3,969,540 A | 7/1976 | Jensen |
| 4,172,972 A | 10/1979 | Ashmead |
| 4,830,716 A * | 5/1989 | Ashmead ..................... 204/72 |
| 5,162,369 A | 11/1992 | Ashmead et al. |
| 5,270,297 A | 12/1993 | Paul et al. |
| 5,292,538 A | 3/1994 | Paul et al. |
| 5,292,729 A | 3/1994 | Ashmead |
| 5,516,925 A | 5/1996 | Pedersen et al. |
| 5,596,016 A | 1/1997 | Ashmead et al. |
| 5,614,553 A | 3/1997 | Ashmead et al. |
| 6,114,379 A | 9/2000 | Wheelwright et al. |
| 6,159,530 A | 12/2000 | Christiansen et al. |
| 6,166,071 A | 12/2000 | Ashmead et al. |
| 6,207,204 B1 | 3/2001 | Christiansen et al. |

OTHER PUBLICATIONS

Solubility Data, as compiled by Chemical Abstracts Service, for the following: Calcium sulfate, Copper (II) sulfate, Zinc (II) sulfate, Iron (III) sulfate, Iron (II) Sulfate, Chromium (III) sulfate, Manganese (IV) sulfate, Magnesium sulfate.*

CRC Handbook of Chemistry and Physics (1973 edition). Robert Weast, PhD, editor. CRC Press. p. B–232.*

R. G. Bineev, et al., "The Biological Activity of Chelates of 3d–Elements With Methionine," *Ozdorovitel'nye Meropriyatiya Prom. Zhivotnovod. Kompleksakh Infekts. Zabol.*, 71–6, 1983.

D. N. Sen, et al., "Infrared Absorption Spectra of Inorganic Coordination Complexes. I. The Nature of Chelation Bonding in Bis(glycino)–copper(II) Monohydrate and Bis–(glycino)–nickel(II) Dihydrate," Journal of the American Chemical Society, vol. 77, pp. 211–212, Jan. 5, 1955.

A. J. Stosick, "The X–Ray Investigation of Copper dl–α–Aminobutyrate," J. Am. Chem. Soc., vol. 67, pp. 362–365, Mar., 1945.

P. A. Kober and K. Sugiura, The Copper Complexes of Amino Acids, Peptides and Peptones, *The Journal of Biological Chemistry*, vol. 13, No. 1, pp. 1–13, 1912.

P. A. Kober and K. Sugiura "The Copper Complexes of Amino Acids, Peptides and Peptones," *American Chemical Journal*, vol. 48, No. 5, pp. 383–411, Nov. 1912.

*Advances In Protein Chemistry*, edited by C. B. Anfinsen, Jr., M. L. Anson, J. T. Edsall, and F. M. Richards, vol. 22, Academic Press, New York, pp. 269–270, 391, 1967.

A. M. Mathieson and H. K. Welsh, "The Crystal Structure of Copper Proline Dihydrate," *Acta Cryst.*, vol. 5, pp. 599–604, 1952.

D. Van Der Helm and W. A. Franks, "The Crystal Structure of Bis(L–serinato)copper(II)," *Acta Cryst.*, vol. B25, pp. 451–457, 1969.

C. M. Weeks, et al., "The Crystal Structure of the Copper(ii) Complex of L–Isoleucine," *Acta Cryst.*, vol. 25, pp. 443–450, 1969.

B. W. Low, et al., "Glycinate Complexes of Zinc and Cadmium," *J. Am. Chem. Soc.*, vol. 81, pp. 4412–4416, 1959.

D. Van Der Helm, et al., "The Crystal Structure of Bis(L–serinato)zinc," *Acta Cryst.*, vol. 26, pp. 1172–1178, 1970.

A. J. Saraceno, et al., "Infrared Absorption Spectra of Inorganic Coordination Complexes. XVI. Infrared Studies of Glycino–Metal Complexes," *J. Am. Chem. Soc.*, vol. 80, pp. 5018–5021, 1958.

J. V. Dubsky and A. Rabas, "A contribution to the study of the formation of salts with glycine," *Spisy vydavane priordovedeckou Fakultou Masarykovy Univ.*, No. 123, 3–18, 1930; cf. C.A.., vol. 24, 4722.

R. J. Hooper, et al, "Infrared Absorption Spectra of Metal–Amino Acid Complexes. IV, The Infrared Spectra and Configurations of Metal–Isoleucine Chelates," *Inorganic Chemistry*, vol. 3, No. 11, pp. 1568–1573, 1964.

(List continued on next page.)

*Primary Examiner*—Paul J. Killos
*Assistant Examiner*—Zachary Tucker
(74) *Attorney, Agent, or Firm*—Thorpe North & Western LLP

(57) ABSTRACT

The present invention relates to compositions and methods of preparing amino acid chelates that are electrically neutral and free of interfering ions. The composition is prepared by reacting in an aqueous solution a calcium oxide and/or hydroxide, an amino acid, and a soluble metal sulfate salt at a ratio sufficient to allow substantially all of the ions present in solution to react forming a metal amino acid chelate and an essentially inert calcium sulfate, and wherein the metal amino acid chelate has a ligand to metal molar ratio from 2:1 to 3:1.

30 Claims, No Drawings

OTHER PUBLICATIONS

C. Neuberg, et al., "Heavy–Metal Hydroxides in *Statu Nascendi* as Reagents for the Purification of Amino Acid Mixtures and the Preparation of Pure Heavy–Metal Salts of Individual Amino Acids," *Arch. Biochem.*, vol. 26, pp. 77–84, 1950.

A. W. Herlinger, et al., "Infrared Spectra of Amino Acids and Their Metal Complexes. II. Geometrical Isomerism in Bis(amino acidato)copper(II) Complexes," *J. Am. Chem. Soc.*, 92:22, pp. 6474, 1970.

A. J. Stosick, "The Crystal Structure of Nickel Glycine Dihydrate," J. Am. Chem. Soc., vol. 67, pp. 365–370, Mar. 1945.

T. Sakurai, et al., "Bis(L–histidinato)nickel(II) Monohydrate," *Acta Cryst.*, B34, pp. 660–662, 1978.

P. L. Meredith and R. A. Palmer, "Polarized Crystal Spectra of Bis(DL–histidinato)nickel(II) Monohydrate and Bis(L–histidinato)nickel(II) Monohydrate," *Inorganic Chemistry*, vol. 10, No. 5, pp. 1049–1056, 1971.

D. Van Der Helm and M. Bilayet Hossain, "The Crystal Structure of Diaquobis(L–serinato)nickel (II)," *Acta Cryst.*, B25, pp. 457, pp. 457–463, 1969.

T. J. Kistenmacher and D. J. Szalda, "Glycylglycinatocopper(II) Dihydrate," *Acta Cryst.*, B31, pp. 1659–1662, 1975.

D. Van Der Helm, et al., "The Crystal and Molecular Structure of the Copper (II) Chelate of L–Leucyl–L–tyrosine," *Acta Cryst.*, B31, pp. 1013–1018, 1975.

W. A. Franks and D. Van Der Helm, "The Crystal and Molecular Structure of the Dimeric Copper(II) Chelate of Glycl–L–leucyl–L–tyrosine," *Acta Cryst.*, B33, pp. 3505–3510, 1977.

P. De Meester and D.J. Hodgson, "The Crystal and Molecular Structure of Clycyl–L–histidyl–glycinatocopper(II) Dihemihydrate," *Acta Cryst.*, B33, pp. 3505–3510, 1977.

Andreas Rosenberg, "The Infra–Red Absorption Spectra of Some Amide– and Dipeptide–Metal Chelates," *Acta Chemica Scandinavica*, vol. 11, No. 8, pp. 1390–1404, 1957.

R. Strandberg, et al., "The crystal structure of copper(II)monoglycyiglycine trihydrate $Cu(NH_2CH_2CONCH_2COO) \cdot 3H_2O$," *Zeitscrift fur Kristallographie*, Bd. 116, pp. 266–289, 1961.

A. R. Manyak, et al., "Metal Chelate Compounds of Glycylglycine and Glycylglycylglycine," *Archives of Biochemistry and Biophysics*, vol. 59, pp. 373–382, 1955.

H. C. Freeman and J. T. Szymanski, "Crystallographic Studies of Metal–Peptide Complexes. V. (β–Alanyl–L–histidinato)copper(II) Dihydrate," *Acta Cryst.*, vol. 22, pp. 406–417, 1967.

C. A. Bear and H. C. Freeman, "Crystallographic Studies of Metal–Peptide Complexes. VII. Glycyl–L–methioninatocopper(II)," *Acta Cryst.*, B32, pp. 2534–3526, 1976.

Andreas Rosenberg, "The Infra–Red Absorption Spectra of Some Amino Acid–Metal Chelates at Liquid Air Temperature," *Acta Chemica Scandinavica*, vol. 10, pp. 840–851, 1956.

Kazuo Nakamoto, *Infrared Spectra of Inorganic Coordination Compounds*, 2d ed., Wiley–Interscience, pp. 232–239, 1970.

* cited by examiner

COMPOSITION AND METHOD FOR PREPARING ELECTRICALLY NEUTRAL AMINO ACID CHELATES FREE OF INTERFERING IONS

FIELD OF THE INVENTION

The present invention relates to compositions and methods of preparing amino acid chelates that are electrically neutral and essentially free of interfering ions. The composition is prepared by reacting, in an aqueous solution, a calcium oxide and/or hydroxide, an amino acid, and a soluble metal sulfate salt at a ratio sufficient to allow substantially all of the ions present in solution to react forming a metal amino acid chelate, an essentially inert calcium sulfate salt, and water. The metal amino acid chelates of the present invention have a ligand to metal molar ratio from about 2:1 to 3:1.

BACKGROUND OF THE INVENTION

Amino acid chelates are generally produced by the reaction between α-amino acids and metal ions having a valence of two or more to form a ring structure. In such a reaction, the positive electrical charge of the metal ion is neutralized by the electrons available through the carboxylate or free amino groups of the α-amino acid.

Traditionally, the term "chelate" has been loosely defined as a combination of a metallic ion bonded to one or more ligands forming heterocyclic ring structures. Under this definition, chelate formation through neutralization of the positive charges of the divalent metal ions may be through the formation of ionic, covalent, or coordinate covalent bonding. An alternative and more modern definition of the term "chelate" requires that the metal ion be bonded to the ligand solely by coordinate covalent bonds forming a heterocyclic ring. In either case, both definitions describe a metal ion and a ligand forming a heterocyclic ring.

A chelate is a definite structure resulting from precise requirement of synthesis. Proper conditions must be present for chelation to take place, including proper mole ratios of ligands to metal ions, pH, and solubility of reactants. For chelation to occur, all components are (generally dissolved in solution and are either ionized or of appropriate electronic configuration in order for coordinate covalent bonding and/or ionic bonding between the ligand and the metal ion to occur.

Chelation can be confirmed and differentiated from mixtures of components by infrared spectra through comparison of the stretching of bonds or shifting of absorption caused by bond formation. As applied in the field of mineral nutrition, there are two allegedly "chelated" products which are commercially utilized. The first is referred to as a "metal proteinate." The American Association of Feed Control officials (AAFCO) has defined a "metal proteinate" as the product resulting from the chelation of a soluble salt with amino acids and/or partially hydrolyzed protein. Such products are referred to as the specific metal proteinate, e.g., copper proteinate, zinc proteinate, etc. Sometimes, metal proteinates are even referred to as amino acid chelates, though this characterization is not accurate. This is because by definition, a metal proteinate must contain partially hydrolyzed proteins which may or may not be mixed with amino acids.

The second product, referred to as an "amino acid chelate," when properly formed, is a stable product having one or more five-membered rings formed by a reaction between the carboxyl oxygen, and the α-amino group of an α-amino acid with the metal ion. Such a five-membered ring is defined by the metal atom, the carboxyl oxygen, the carbonyl carbon, the α-carbon and the α-amino nitrogen. The actual structure will depend upon the ligand to metal mole ratio and whether the carboxyl oxygen forms a coordinate covalent bond or an ionic bond with the metal ion. Generally, the ligand to metal molar ratio is at least 1:1 and is preferably 2:1 or 3:1. However, in certain instances, the ratio may be 4:1. Most typically, an amino acid chelate may be represented at a ligand to metal molar ratio of 2:1 according to Formula 1 as follows:

Formula 1

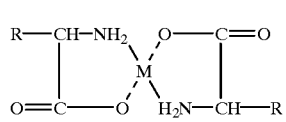

In the above formula, the dashed lines represent coordinate covalent bonds, covalent bonds, or ionic bonds. The solid lines between the α-amino group and the metal (M) are covalent or coordinate covalent bonds. Further, when R is H, the amino acid is glycine which is the simplest of the α-amino acids. However, R could be a radical forming any other of the other twenty or so naturally occurring amino acids derived from proteins. All of the amino acids have the same configuration for the positioning of the carboxyl oxygen and the α-amino nitrogen with respect to the metal ion. In other words, the chelate ring is defined by the same atoms in each instance, even though the R group may vary.

The American Association of Feed Control Officials (AAFCO) have also issued a definition for amino acid chelates. It is officially defined as the product resulting from the reaction of a metal ion from a soluble metal salt with amino acids having a mole ratio of one mole of metal to one to three (preferably two) moles of amino acids to form coordinate covalent bonds. The average weight of the hydrolyzed amino acids must be approximately 150 and the resulting molecular weight of the chelate must not exceed 800. The products are identified by the specific metal forming the chelate, e.g., iron amino acid chelate, copper amino acid chelate, etc. The reason a metal atom can accept bonds over and above the oxidation state of the metal is due to the nature of chelation.

For example, at the α-amino group of an amino acid, the nitrogen contributes both of the electrons used in the bonding. These electrons fill available spaces in the d-orbitals forming a coordinate covalent bond. Thus, a metal ion with a normal valency of +2 can be bonded by four bonds when fully chelated.

In this state, the chelate is completely satisfied by the bonding electrons and the charge on the metal atom (as well as on the overall molecule) is zero. As stated previously, it is possible that the metal ion be bonded to the carboxyl oxygen by either coordinate covalent bonds or ionic bonds. However, the metal ion is typically bonded to the α-amino group by coordinate covalent bonds only.

Amino acid chelates can also be formed using small peptide ligands instead of single amino acids. These will usually be in the form of dipeptides, tripeptides, and sometimes tetrapeptides because larger ligands have molecular weights that are too great for direct cellular assimilation of the chelate formed.

Generally, peptide ligands will be derived by the hydrolysis of protein. However, peptides prepared by conventional synthetic techniques or genetic engineering can also be used.

When a ligand is a di- or tripeptide, a radical of the formula [C(O)CHRNH]$_e$ H will replace one of the hydrogens attached to the nitrogen atom in Formula 1. R, as defined in Formula 1, can be H or the residue of any other naturally occurring amino acid and e can be an integer of 1, 2 or 3. When e is 1 the ligand will be a dipeptide, when e is 2 the ligand will be a tripeptide and so forth.

The structure, chemistry and bioavailability of amino acid chelates is well documented in the literature, e.g. Ashmead et al., Chelated Mineral Nutrition, (1982), Chas. C. Thomas Publishers, Springfield, Ill.; Ashmead et al., Intestinal Absorption of Metal Ions, (1985), Chas. C. Thomas Publishers, Springfield, Ill.; Ashmead et al., Foliar Feeding of Plants with Amino Acid Chelates, (1986), Noyes Publications, Park Ridge, N. J.; U.S. Pat. Nos. 4,020,158; 4,167,564; 4,216,143; 4,7216,44; 4,599,152; 4,774,089; 4,830,716; 4,863,898; 4,725,427; and others, the entire teachings of which are incorporated by reference.

One advantage of amino acid chelates in the field of mineral nutrition is attributed to the fact that these chelates are readily absorbed in the absorptive mucosal cells or plant cells by means of active transport or other know mechanisms. In other words, the minerals are absorbed along with the amino acids as a single unit utilizing the amino acids as carrier molecules. Therefore, the problems associated with the competition of ions for active sites and the suppression of specific nutritive mineral elements by others are avoided. This is especially true for compounds such as iron sulfates that must be delivered in relatively large quantities in order for the body or plant to absorb an appropriate amount. This is significant because large quantities often cause nausea and other gastrointestinal discomforts in animals as well as create an undesirable taste. Additionally, in plants, large amounts of these compounds can act to burn leaves and cause other undesirable results.

In the past, amino acid chelates have generally been made by first dissolving a water soluble metal salt in water. An amino acid ligand is then reacted with the metal ion at a ratio of ligand to metal from 1:1 to 4:1, preferably 2:1. Often, the ligand is a hydrolysis product obtained by acid, base, base-acid, base-acid-base, or enzyme hydrolysis. In such cases, the by products from hydrolysis, such as anions including chlorides, sulfates, phosphates and nitrates, and cations including potassium and sodium, remain in the hydrolysate. Reaction products of metal salts with proteins or with acid and/or base hydrolyzed proteins are taught in U.S. Pat. Nos. 2,960,406; 3,396,104; 3,463,858; 3,775,132; 4,020,158; 4,103,003; and 4,172,072.

In fact, most water soluble salts used in making amino acid chelates have been either sulfates or chlorides. Using the sulfate ion as exemplary, the reaction has generally proceeded

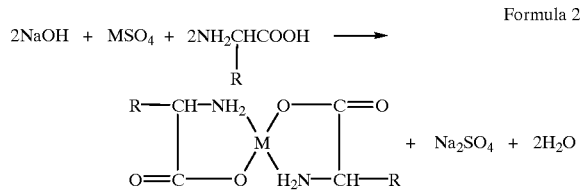

Formula 2 where M is a bivalent metal cation and R is a radical of a naturally occurring amino acid, dipeptide or polypeptide. It is apparent from the above formula that the sulfate anion is present in the reaction mixture in the form of sodium sulfate.

U.S. Pat. No. 2,877,253 teaches a product formed by the reaction of one mole of glycine with one mole of ferrous sulfate. That patent indicates that the sulfate anion becomes tied up in the reaction which allegedly forms a ferrous sulfate-glycine complex. Whether the sulfate actually participates in the reaction or is merely present as the salt of an alkali metal, it nevertheless is present in the reaction mixture. Thus, in many cases, the sulfate interferes with the total reaction and art absorption of the chelate. Such products are difficult to purify. While sodium sulfate, per se, is water soluble, the reaction between a metal sulfate and an amino acid is never carried to 100% completion and the sulfate ion is always present. The same holds true for the presence of chloride ions when utilizing a metal chloride salt for amino acid chelate preparation.

Even if one were to attempt to wash out the excess sulfate or chloride ions with repeated washes, such an attempt would likely be counter productive inasmuch as glycine and other amino acid ligands are also soluble to a degree. Hence, depending upon pH, the unreacted ligands or weakly held ligands could also be removed along with the unwanted anions.

As mentioned, in order to manufacture amino acid chelates, it generally requires that the metal salt and the ligand both be dissolved in water. One problem with this is employing metal salts that are soluble but essentially free from anions that can interfere with the chelation process. This is the subject of U.S. Pat. Nos. 4,599,152 and 4,830, 716, both of which are incorporated by reference.

In the past, if certain soluble metal salts, such as sulfates, were used as a mineral source for chelation purposes, the resulting anions interfered with the chelation process. For example, the attraction between the lone pair of electrons on the amine group of an amino acid and a hydrogen ion is strong. This is why glycine is represented by the zwitterionic structure $^+H_3NCH_2COO^-$. This strong attraction for the hydrogen ion explains why amino acids are weak acids, e.g., the glycine is not easily deprotonated. In water, only about 0.5% of the glycine typically disassociates and releases a hydrogen ion. Additionally, in the prior art, the introduction of mineral acid salts into solution, such as copper sulfate, resulted in the creation of copper ions which compete with the hydrogen ion for the lone pair of electrons on the NH$_2$group. Unfortunately, the equilibrium favors the majority of the amino groups remaining protonated. Thus, in order to efficiently chelate metal ions from certain soluble salts, it becomes desirable to render the interfering ions inactive or use soluble metal salts with non-interfering ions, such as oxides or hydroxides.

SUMMARY OF THE INVENTION

The present invention comprises compositions and methods of manufacturing electrically neutral amino acid chelates free of interfering ions. These amino acid chelates are prepared by reacting an calcium oxide and/or hydroxide, an amino acid, and a soluble metal sulfate salt in an aqueous solution at a ratio sufficient to allow substantially all of the ions present in solution to react. Thus, a metal amino acid chelate, calcium sulfate, and water are formed without the presence of any significant amounts of interfering ions. The metal amino acid chelates produced will have a ligand to metal molar ratio from about 2:1 to 3:1, depending on the valency of the metal, e.g., Fe(II) forms 2:1 and Fe(III) forms 3:1.

DETAILED DESCRIPTION OF THE INVENTION

Before the present invention is disclosed and described, it is to be understood that this invention is not limited to the particular process steps and materials disclosed herein because such process steps and materials may vary somewhat. It is also to be understood that the terminology used herein is used for the purpose of describing particular embodiments only. The terms are not intended to be limiting because the scope of the present invention is intended to be limited only by the appended claims and equivalents thereof.

It must be noted that, as used in this specification and the appended claims, the singular forms "a," "an," and "the" include plural referents unless the content clearly dictates otherwise.

"Electrically neutral" refers to the final product of the reaction in which essentially all of the reactants have formed product such that there is no net charge, i.e., the amino acid chelate in particular is uncharged.

"Interfering ion" is meant to include any cation or anion which would hinder the formation of the amino acid chelate and which remains in the composition as a charged ion that has not reacted to form an amino acid chelate, calcium sulfate, or water.

"Metal amino acid chelate" or "amino acid chelate" shall include metal ions bonded to amino acid ligands forming heterocyclic rings. The bonds may be coordinate covalent, covalent and/or ionic at the carboxyl oxygen group. However, at the α-amino group, the bond is typically a coordinate covalent bond. Preferred amino acids include all of the naturally occurring amino acids.

"Metal" is meant to cover all nutritionally relevant metals that are more soluble as sulfate salts that calcium sulfate. Though calcium is a metal, for purposes of the present disclosure, calcium is excluded within this definition unless the context clearly dictates otherwise.

"Soluble metal sulfate" or "soluble metal sulfate salt" include all divalent or trivalent metals that are more soluble than calcium sulfate when in the form of a sulfate salt. Preferred soluble metal sulfate salts are comprised of at least one nutritionally relevant metal.

"Nutritionally relevant metals" include metals that are known to be needed by living organisms, particularly plants and mammals, including humans. Metals such as copper (Cu), zinc (Zn), iron (Fe), cobalt (Co), magnesium (Mg), manganese (Mn), and/or chromium (Cr), among others, are exemplary of nutritionally relevant metals.

Essentially, the present invention includes compositions and methods of manufacturing electrically neutral amino acid chelates free of interfering ions. These chelates are prepared by reacting 1) calcium oxide and/or hydroxide, 2) one or more amino acid, and 3) a soluble metal sulfate salt in an aqueous solution at a ratio sufficient to allow substantially all of the ions present in solution to react forming a metal amino acid chelate, calcium sulfate, and water, and wherein the metal amino acid chelate has a ligand to metal molar ratio from about 2:1 to 3:1.

The compositions and methods disclosed herein are similar to the invention described in the patent application filed of even date herewith and having U.S. Ser. No. 09/686,046 filed Oct. 11, 2000 which is incorporated herein by reference. A major difference between the present invention and that disclosed in the U.S. Ser. No. 09/686,046 application is that in the present invention, the amino acid chelates themselves are electrically neutral (not charged) and have a ligand to metal molar ratio from about 2:1 to 3:1. The U.S. Ser. No. 09/686,046 application discloses compositions and methods of preparing amino acid chelates that are charged having a hydroxide counter ion, and which have a ligand to metal molar ratio from about 1:1 to 2:1.

The amino acid to be used in the present invention is preferably one or more of the naturally occurring amino acid selected from the group consisting of alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine, valine, and combinations thereof. However, dipeptides, tripeptides, and tetrapeptides formed by any combination of the naturally occurring amino acids can also be used. The metal should be more soluble as a sulfate salt than calcium sulfate. Exemplary metals include those selected from the group consisting of Cu, Zn, Fe, Cr, Co, Mg, Mn, and combinations thereof. Therefore, the metal reactant is preferably provided as a sulfate salt selected from the group consisting of copper sulfate ($CUSO_4$), zinc sulfate ($ZnSO_4$), ferrous sulfate ($FeSO_4$), manganese sulfate ($MnSO_4$), cobalt sulfate ($COSO_4$), magnesium sulfate ($MgSO_4$), ferric sulfate [$Fe_2(SO_4)_3$], chromic sulfate [$Cr_2(SO_4)_3$], and combinations thereof.

While not wanting to be bound by any theory, possible mechanism describing the reaction by which the amino acid chelates of the present invention are prepared may be broken down into two steps. Step A involves the reaction of one or more amino acids with a soluble calcium oxide and/or hydroxide in an aqueous solution forming a calcium amino acid chelate or complex product. Step B involves the reaction of a soluble metal sulfate salt with the calcium amino acid chelate or complex product formed in Step A. The calcium is displaced by the metal forming a metal amino acid chelate having a ligand to metal molar ratio from 2:1 to 3:1. Further, the calcium reacts with the sulfate anion to form an inert and highly insoluble calcium sulfate precipitate.

The reactions used to prepare electrically neutral amino acid chelates essentially free of interfering ions and having a ligand to metal molar ratio from about 2:1 to 3:1 are shown below. Formulas 3a and 3b illustrate the production of an amino acid chelate having a 2:1 ligand to metal molar ratio:

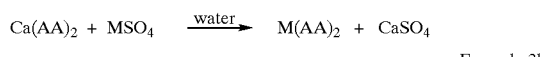
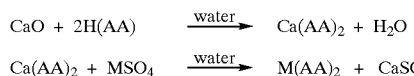
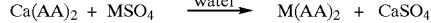

In Formulas 3a and 3b above and 4a and 4b below, H(AA) is an amino acid selected from the group consisting of naturally occurring amino acids and combinations thereof. H, when disassociated from AA, is a hydrogen ion donor from the carboxyl group present on the amino acid. M is a nutritionally relevant metal having a valency of +2 (excluding calcium) such as Cu, Zn, Fe, Co, Mg, and/or Mn.

To illustrate this mechanism further, consider the reactants copper sulfate, calcium oxide, and glycine. First, one mole of calcium oxide is reacted with two moles of glycine. After allowing the calcium and glycine to react, copper sulfate is added. The log of the equilibrium constant at zero ionic strength for the reaction $Ca^{2+}+(Gly)^-\rightleftharpoons Ca(Gly)^+$, where $(Gly)^-$ represents a glycine anion, is 1.39. By comparison, for the same reaction with copper rather than calcium, the log of the equilibrium constant is 8.56. Though a literature value is not given for the equilibrium constant for the attachment of two glycinate anions to a calcium cation, the principle that copper has stronger affinity for glycine ligands than does calcium is demonstrated by these values.

It is important to note that the reactants, i.e., CaO, H(AA), and $MSO_4$, may be added in any order. For example, all three reactants may be added simultaneously or the amino acid and the soluble metal salt may be added before the calcium oxide or hydroxide. However, it is important to note that the above equation must be balanced so that the final products, $M(AA)_2$, $CaSO_4$, and water, are free of interfering ions and is electrically neutral. Therefore, notwithstanding Formula 3a and 3b which illustrates a preferred mechanism, the general formula of the present invention when a 2:1 ligand to metal molar ratio is desired may be represented by Formulas 4a and 4b as follows:

Formula 4a

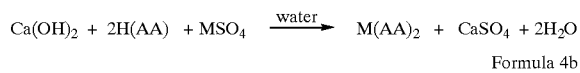

$$Ca(OH)_2 + 2H(AA) + MSO_4 \xrightarrow{water} M(AA)_2 + CaSO_4 + 2H_2O$$

Formula 4b

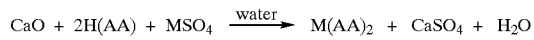

$$CaO + 2H(AA) + MSO_4 \xrightarrow{water} M(AA)_2 + CaSO_4 + H_2O$$

For purposes of the present invention, multiple metals, amino acids, salts, etc., may be used in the context of the present invention as well. However, metals having a proper valency state should be used, e.g., Cu, Zn, Fe(II), Co, Mg, Al and/or Mn for amino acid chelates having a ligand to metal molar ratio of about 2:1.

General Formula 4 above may be modified to prepare amino acid chelates having a ligand to metal molar ratio of about 3:1 using metals having a valency of +3, e.g., Fe(III), Cr, etc. The general formula of the present invention when a 3:1 ligand to metal molar ratio is desired may be represented by Formulas 5a, and 5b as follows:

Formula 5a

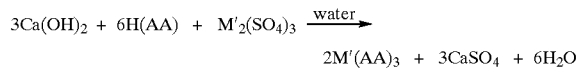

$$3Ca(OH)_2 + 6H(AA) + M'_2(SO_4)_3 \xrightarrow{water}$$
$$2M'(AA)_3 + 3CaSO_4 + 6H_2O$$

Formula 5b

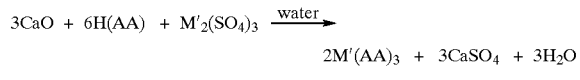

$$3CaO + 6H(AA) + M'_2(SO_4)_3 \xrightarrow{water}$$
$$2M'(AA)_3 + 3CaSO_4 + 3H_2O$$

In Formulas 5a and 5b, H(AA) is an amino acid selected from the group consisting of naturally occurring amino acids and combinations thereof. H, when disassociated from AA, is a hydrogen ion donor from the carboxyl group present on the amino acid. M' is a nutritionally relevant metal having a valence of +3 such as Fe(III) and/or Cr.

It is important to note that though the compositions and methods of the present invention provide electrically neutral amino acid chelates free of interfering ions, calcium sulfate is always a byproduct. Therefore, the calcium sulfate may be substantially separated out of the compound by methods commonly known in the art while the chelate is still in solution. Alternatively, the calcium sulfate may remain in the compound as a stabilizer or for other purposes.

To cite a specific example of a pure and electrically neutral amino acid chelate having a ligand to metal molar ratio of about 2:1, the following reactions steps may be followed. First, one mole of calcium oxide (CaO) may be reacted with two moles of glycine to form a reaction product of calcium bisglycinate in water. The problems associated with a hydrogen ion being bound to the amine group are resolved because it has reacted with the oxygen from the CaO to form water. To this solution, copper sulfate ($CUSO_4$) is added. This allows for the disassociated copper ions to react with the calcium bisglycinate as the strength of bonding between a metal and a glycinate anion is stronger than the calcium glycinate bond. As such, the calcium is displaced by the copper forming copper bisglycinate. The calcium ions that are displaced in turn react with the sulfate anions (from the $CuSO_4$) forming calcium sulfate which is sparingly soluble and essentially inert.

The present invention also encompasses drying of the chelate solution when appropriate to provide a powder for some uses, e.g., human, animal, and plant nutrition. However, with some applications, it may be desired that the chelate remain in solution, e.g., foliar use. If drying the chelate to form a particulate, any conventional drying technique as is known in the art may be used. For example, if spray drying, bulk density of the powder produced in a spray dryer is affected by the mesh size of the nozzles in the dryer, the pump pressure, and the percent of total solids in the solution to be dried. In general, the higher the total solids, the greater the bulk density of the resulting powder. A greater bulk density also reduces the electrostatic properties of the spray dried powder. For example, the presence of the calcium sulfate (terra alba) suspended in the metal amino acid chelate solution by continual agitation will increase the total solids to be dried, thus, increasing the ultimate bulk density of the dried chelate.

The increased bulk density of the dried product may have at least three distinct advantages. First, the dried product is less hygroscopic due to the increased density and due to the fact that calcium sulfate salt is less hygroscopic than the amino acid chelate, which through the drying process have waters of hydration removed. Second, a more dense particle is less electrostatic. This potentially reduces the cleanup time in a mixer when the chelate is blended with other food or pharmaceutical substances and enhances mixing characteristics when powdered chelates are blended with these other substances. Third, when the amino acid chelate is mixed with calcium sulfate, the presence of calcium sulfate stabilizes the amino acid chelate in an acidic solution.

EXAMPLES

The following examples illustrate methods of preparing amino acid chelates that are electrically neutral and essentially free of interfering ions. The following examples should not be considered as limitations of the present invention, but should merely teach how to make the best known amino acid chelates based upon current experimental data.

Each of the composition examples described herein provide an amount of chelate product produced in solution. However, often, the step of drying, i.e., removing moisture, from a chelate solution may be preferred. Additionally, prior to drying, calcium sulfate (terra alba) may be removed by separation techniques known by those skilled in the art if desired.

Example 1

Preparation of Copper Glycine Amino Acid Chelate

Into about 923 grams of water was dissolved 150.14 grams of glycine. Next, 57.25 grams of calcium oxide, which was about 70% calcium by weight, was added. The solution was continually stirred until all of the calcium oxide was dissolved. This took about 15 minutes. No heat was applied for this particular reaction, though heat could optionally be used in this or other examples. The resulting reaction formed a calcium bisglycinate chelate or complex and water, i.e., the hydrogen ions were removed from the glycine and the oxygen was removed from the calcium oxide.

Next, 254.18 grams of copper sulfate hydrate containing 25% copper by weight was added to the calcium chelate solution. Again, the solution was constantly stirred while the copper sulfate was dissolved. As the copper sulfate went into solution, a white precipitate of calcium sulfate formed. Upon completion of the reaction, about 214 grams of a copper glycine chelate having a ligand to metal molar ratio of 2:1 was formed.

Example 2

Preparation of Zinc Glycine Amino Acid Chelate

About 250 grams of glycine was dissolved into 937.8 grams of water. Once the glycine was significantly dissolved, about 95 grams of calcium oxide was added. The solution was continually stirred for about 15 minutes until all of the calcium was dissolved. The resulting reaction formed a calcium bisglycinate chelate or complex and water.

Next, 299.97 grams of zinc sulfate hydrate containing 35% zinc by weight was added to the calcium chelate solution. Upon constant stirring, the zinc sulfate went into solution and a white precipitate of calcium sulfate formed. About 355 grams of a zinc glycine chelate having a ligand to metal molar ratio of about 2:1 was formed.

Example 3

Preparation of Manganese Glycine Amino Acid Chelate

In about 1000 grams of water was dissolved 203.27 grams of glycine and 76.38 grams of calcium oxide. The solution was continually stirred until all of the calcium oxide was dissolved.

This took about 15 minutes. No heat was applied for this particular reaction. A calcium bisglycinate chelate or complex aqueous solution was formed.

To the calcium bisglycinate chelate solution was added 272.88 grams of manganese sulfate hydrate containing 27% manganese by weight. Again, the solution was constanatly stirred while the manganese sulfate was significantly dissolved. As the anganese sulfate went into solution, a white precipitate of calcium sulfate formed. About 277 grams of a manganese bisglycinate chelate was formed.

Example 4

Preparation of manganese Glycine Amino Acid Chelate

The procedure of Example 3 may be followed using 100.82 grams of calcium hydroxide instead of 76.38 grams calcium oxide with similar results, i.e., about 277 grams of a manganese bisglycinate is formed, though more water is formed in the reaction.

Example 5

Preparation of Magnesium Glycine Amino Acid Chelate

Into about 1500 grams of water was dissolved 155.63 grams of glycine. Next, 58.97 grams of calcium oxide, which was 70% calcium by weight, was also added. The solution was continually stirred until all of the calcium oxide was essentially completely dissolved. Again, no heat was applied to the reaction. A calcium bisglycinate chelate or complex solution containing excess water was formed.

Next, 572.02 grams of magnesium sulfate hydrate containing 9.86% magnesium by weight was added to the calcium chelate solution. The solution was stirred while the magnesium sulfate dissolved and a white precipitate of calcium sulfate formed. About 211 grams of a magnesium glycinate was formed having a 1:1 ligand to metal molar ratio.

Example 6

Preparation of Ferrous Glycine Amino Acid Chelate

Into about 1300 grams of water was dissolved 210.72 grams of glycine and 79.86 grams of calcium oxide. The solution was stirred until all of the calcium oxide appeared to be fully dissolved, i.e., about 15 minutes. The resulting reaction formed a calcium bisglycinate chelate or complex solution.

To the calcium bisglycinate chelate or complex solution was added 381.55 grams of ferrous sulfate hydrate containing 20% ferrous iron by weight. Again, the solution was constantly stirred while the ferrous sulfate dissolved and a white precipitate of calcium sulfate formed. About 287 grams of a ferrous glycine chelate was formed having a ligand to metal molar ratio of about 2:1.

Example 7

Preparation of Zinc Glycine/Methionine Amino Acid Chelate

About 7.00 grams of water used to dissolve 86.5 grams of glycine and 70 grams of DL-methionine. Next, 47 grams of calcium oxide, which was 70% calcium by weight, was added. The solution was continually stirred until all of the calcium oxide appeared to be dissolved. The reaction formed a calcium bisglycinate chelate or complex solution.

Next, 150 grams of zinc sulfate hydrate containing 35.5% zinc by weight was stirred into the calcium chelate solution wherein a white precipitate of calcium sulfate formed as a by product. This process produced about 210 grams of a zinc glycine/methionine chelate having a ligand to metal molar ratio of 2:1.

Example 8

Preparation of Copper, Zinc, and Manganese Amino Acid Chelate Mixture

About 2400 grams of water was used to dissolve 475 grams of glycine. Next, 175 grams of calcium oxide, which was 70% calcium by weight, was stirred into the aqueous solution. The solution was continually stirred for about 15 minutes until all of the calcium oxide was dissolved and a calcium bisglycinate chelate or complex solution was formed.

To the calcium bisglycinate chelate or complex solution was added about 110 grams of copper sulfate hydrate containing 25% copper by weight, 300 grams of zinc sulfate hydrate containing 35% zinc by weight, and 185 grams of manganese sulfate hydrate containing 29% manganese by weight. Again, the solution was ago constantly stirred while the copper sulfate, zinc sulfate, and manganese sulfate were all dissolved and calcium sulfate had in fully precipitated.

This process produced about 661 grams of amino acid chelates comprised of glycine as the ligand and copper, zinc, and/or manganese as the metal. The ligand to metal molar ratio was generally about 2:1.

Example 9

Preparation of Copper, Zinc, Manganese, and Iron Amino Acid Chelate Mixture

To about 2600 grams of water was stirred 455 grams of glycine and 173 grams of calcium oxide. Once the glycine and calcium oxide had dissolved, a calcium bisglycinate chelate or complex solution was formed.

Next, about 10 grams of copper sulfate hydrate containing 25% Cu by weight, 142 grams of zinc sulfate hydrate containing 35% Zn by weight, 65 grams of manganese sulfate hydrate containing 29% Mn by weight, and 500 grams of iron sulfate hydrate containing 20% Fe by weight were added to the calcium chelate solution. Again, the solution was constantly stirred while the copper sulfate, zinc sulfate, manganese sulfate, and ferrous sulfate were dissolved. A calcium sulfate precipitate formed as well as about 626 grams of amino acid chelates comprised of glycine as the ligand and copper, zinc, manganese, and/or iron as the metal. The ligand to metal molar ratio was generally about 2:1.

Example 10

Preparation of Zinc Glycine Amino Acid Chelate

About 250 grams of glycine, about 95 grams of calcium oxide and about 300 grams of zinc sulfate(35.5% zinc by weight) were simultaneously dissolved into 937.8 grams of water. Under no added heat, the solution was continually stirred for about 30 minutes. As the zinc sulfate and the calcium oxide went into solution, a white precipitate of calcium sulfate and about 356 grams of a zinc glycine chelate having a ligand to metal molar ratio of 2:1 was formed.

Example 11

Preparation of Ferrous Glycine Amino Acid Chelate

To about 1300 grams of water was added about 382 grams of ferrous sulfate containing 20%,Fe(II) by weight. The solution was stirred until the ferrous sulfate dissolved. Next, about 211 grams of glycine was stirred into the solution for about 30 minutes. To the aqueous solution was added about 80 grams of calcium oxide. Again the solution was continually stirred until all of the CaO was dissolved. As the calcium oxide went into solution, a white precipitate of calcium sulfate as well as about 287 grams of a ferrous glycine chelate having a ligand to metal molar ratio of 2:1 was formed.

Example 12

Preparation of Chromium Glycine Amino Acid Chelate

About 2252 grams of water was used to dissolve 450.42 grams of glycine and 168.24 grams of calcium oxide into solution. The resulting reaction formed a calcium trisglycinate chelate or complex solution.

Next, 500.18 grams of chromic sulfate hydrate containing 19% chromium by weight was added to the calcium chelate solution. The solution was stirred while the copper sulfate was dissolved and as a white precipitate of calcium sulfate formed. Upon completion of the reaction, about 545 grams of a chromic trisglycinate chelate having a ligand to metal molar ratio of about 3:1 was formed.

Example 13

Preparation of Chromium Glycine Amino Acid Chelate

The procedure of Example 12 may be followed using 222.08 grams of calcium hydroxide instead of 168.24 grams calcium oxide with similar results, i.e., about 545 grams of a chromic trisglycinate is formed.

Example 14

Comparison Between Amino Acid Chelates and Amino Acid Chelates in the Presence of Terra Alba A 10:1 mixture of copper bisglycinate to terra alba ($CaSO_4$) [Sample 1] was prepared and shaken together in a plastic bag. Next, a pure copper bisglycinate without the presence of terra alba [Sample 2] was also prepared and shaken in a plastic bag. With regard to Sample 1, no particulates stuck to the walls of the bag. Conversely, with Sample 2, a blue hazei of product stuck the walls of the bag. This demonstrated that Sample 1 was less electrostatic.

Sample 1 was further compared to Sample 2 by rubbing a portion of each between the thumb and finger. Sample 2 quickly balled up with moisture from the thumb and finger as well as from the surrounding air. Conversely, Sample 1 did not ball up. This demonstrated that Sample 1 was less hygroscopic.

The particle size found in Sample 1 and Sample 2 was about 70 mesh. Thus, the presence of terra alba did not significantly change the particle size.

Finally, Sample 2 was added to a stimulated gastric solution which caused the product to change color. Sample 1 was similarly added to a stimulated gastric solution. However, no color change was observed demonstrating the stabilizing effect of terra alba sag on an amino acid chelate in an acid solution.

While the invention has been described with reference to certain preferred embodiments, those skilled in the art will appreciate that various modifications, changes, omissions, and substitutions can be made without departing from the spirit of the invention. It is intended, therefore, that the invention be limited only by the scope of the following claims.

We claim:

1. A method of preparing electrically neutral amino acid chelates free of interfering ions comprising reacting in an aqueous solution
    a) a calcium oxide or hydroxide,
    b) an amino acid, and
    c) a soluble metal sulfate salt at a ratio sufficient to allow substantially all of the reactants present in solution to react forming an electrically neutral metal amino acid chelate, and calcium sulfate, and wherein said metal amino acid chelate has a ligand to metal molar ratio from 2:1 to 3:1.

2. A method as in claim 1 wherein the metal is divalent and the ligand to metal molar ratio is about 2:1.

3. A method as in claim 1 wherein the metal is trivalent and the ligand to metal molar ratio is about 3:1.

4. A method as in claim 1 wherein said amino acid is selected from the group consisting of alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine, valine, and combinations thereof, and dipeptides, tripeptides, and tetrapeptides formed by any combination of said amino acids thereof.

5. A method as in claim 1 wherein said metal is a divalent or trivalent cation selected from the group consisting of Cu, Zn, Fe, Cr, Co, Mg, Mn, and combinations thereof.

6. A method as in claim 1 wherein said soluble metal sulfate salt is a member selected from the group consisting $CUSO_4$, $ZnSO_4$, $FeSO_4$, $CoSO_4$, $MnSO_4$, $MgSO_4$, $Fe_2(SO_4)_3$, $Cr_2(SO_4)_3$, and combinations thereof.

7. A method as in claim 1 wherein said amino acid is glycine and said metal amino acid chelate is selected from the group consisting of copper glycinate, zinc glycinate, iron glycinate, iron bisglycinate, chromium bisglycinate, cobalt glycinate, magnesium glycinate, manganese glycinate, and combinations thereof.

8. A method as in claim 1 wherein said metal amino acid chelate has a ligand to metal molar ratio of about 2:1 and the reaction is further defined by:

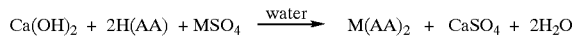

where H(AA) is one or more naturally occurring amino acids; H when disassociated from AA is a hydrogen ion donor from the carboxyl group present on the amino acid; and M is selected from the group consisting of Cu, Zn, Fe, Co, Mg, Mn, and combinations thereof.

9. A method as in claim 1 wherein said metal amino acid chelate has a ligand to metal molar ratio of about 2:1 and the reaction is further defined by:

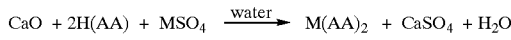

where H(AA) is one or more naturally occurring amino acids; H when disassociated from AA is a hydrogen ion donor from the carboxyl group present on the amino acid; and M is selected from the group consisting of Cu, Zn, Fe, Co, Mg, Mn, and combinations thereof.

10. A method as in claim 1 wherein said metal amino acid chelate has a ligand to metal molar ratio of about 3:1 and the reaction is further defined by:

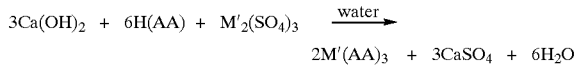

where H(AA) is one or more naturally occurring amino acids; H when disassociated from AA is a hydrogen ion donor from the carboxyl group present on the amino acid; and M' is selected from the group consisting of Fe, Cr, and combinations thereof.

11. A method as in claim 1 wherein said metal amino acid chelate has a ligand to metal molar ratio of about 3:1 and the reaction is further defined by:

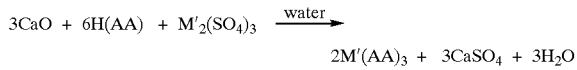

where H(AA) is one or more naturally occurring amino acids; H when disassociated from AA is a hydrogen ion donor from the carboxyl group present on the amino acid; and M' is selected from the group consisting of Fe, Cr, and combinations thereof.

12. A method as in claim 1 wherein said calcium sulfate is substantially separated out.

13. A method as in claim 1 wherein said calcium sulfate is not separated out.

14. A method as in claim 1 further comprising a subsequent step of drying the metal amino acid chelate and the calcium sulfate.

15. An electrically neutral amino acid chelate free of interfering ions admixed with calcium sulfate prepared by reacting in an aqueous solution a) a calcium oxide or hydroxide, b) an amino acid, and c) a soluble metal sulfate salt at a ratio sufficient to allow substantially all of the ions present in solution to react forming an electrically neutral metal amino Acid Chelate, and calcium sulfate, and wherein said metal amino Acid Chelate has a ligand to metal molar ratio from 2:1 to 3:1.

16. An amino acid chelate as in claim 15 wherein the metal is divalent and the ligand to metal molar ratio is about 2:1.

17. An amino acid chelate as in claim 15 wherein the metal is trivalent and the ligand to metal molar ratio is about 3:1.

18. An amino acid chelate as in claim 15 wherein said amino acid is selected from the group consisting of alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine, valine, and combinations thereof, and dipeptides, tripeptides, and tetrapeptides formed by any combination of said amino acids thereof.

19. An amino acid chelate as in claim 15 wherein said metal is a divalent or trivalent cation selected from the group consisting of Cu, Zn, Fe, Cr, Co, Mg, Mn, and combinations thereof.

20. An amino acid chelate as in claim 15 wherein said soluble metal sulfate salt is a member selected from the group consisting $CuSO_4$, $ZnSO_4$, $FeSO_4$, $CoSO_4$, $MnSO_4$, $MgSO_4$, $Fe_2(SO_4)_3$, $Cr_2(SO_4)_3$, and combinations thereof.

21. An amino acid chelate as in claim 15 wherein said amino acid is glycine and said metal amino acid chelate is selected from the group consisting of copper glycinate, zinc glycinate, iron glycinate, iron bisglycinate, chromium bisglycinate, cobalt glycinate, magnesium glycinate, and combinations thereof.

22. An amino acid chelate as in claim 15 wherein said metal amino acid chelate has a ligand to metal molar ratio of about 2:1 and the preparation thereof is further defined by:

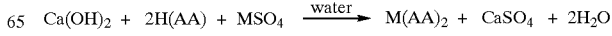

where H(AA) is one or more naturally occurring amino acids; H when disassociated from AA is a hydrogen ion donor from the carboxyl group present on the amino acid; and M is selected from the group consisting of Cu, Zn, Fe, Co, Mg, Mn, and combinations thereof.

23. An amino acid chelate as in claim 15 wherein said metal amino acid chelate has a ligand to metal molar ratio of about 2:1 and the preparation thereof is further defined by:

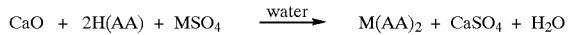

$$CaO + 2H(AA) + MSO_4 \xrightarrow{water} M(AA)_2 + CaSO_4 + H_2O$$

where H(AA) is one or more naturally occurring amino acids; H when disassociated from AA is a hydrogen ion donor from the carboxyl group present on the amino acid; and M is selected from the group consisting of Cu, Zn, Fe, Co, Mg, Mn, and combinations thereof.

24. An amino acid chelate as in claim 15 wherein said metal amino acid chelate has a ligand to metal molar ratio of about 3:1 and the preparation thereof is further defined by:

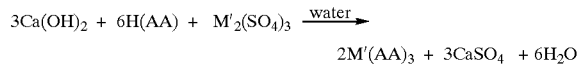

$$3Ca(OH)_2 + 6H(AA) + M'_2(SO_4)_3 \xrightarrow{water} 2M'(AA)_3 + 3CaSO_4 + 6H_2O$$

where H(AA) is one or more naturally occurring amino acids; H when disassociated from AA is a hydrogen ion donor from the carboxyl group present on the amino acid; and M' is selected from the group consisting of Fe, Cr, and combinations thereof.

25. An amino acid chelate as in claim 15 wherein said metal amino acid chelate has a ligand to metal molar ratio of about 3:1 and the preparation thereof is further defined by:

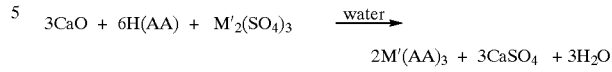

$$3CaO + 6H(AA) + M'_2(SO_4)_3 \xrightarrow{water} 2M'(AA)_3 + 3CaSO_4 + 3H_2O$$

where H(AA) is one or more naturally occurring amino acids; H when disassociated from AA is a hydrogen ion donor from the carboxyl group present on the amino acid; and M' is selected from the group consisting of Fe, Cr, and combinations thereof.

26. An amino Acid Chelate as in claim 15 which has been recovered in dry form.

27. An amino acid chelate as in claim 15 wherein the metal is divalent and the ligand to metal molar ratio is about 2:1.

28. An amino acid chelate as in claim 15 wherein the metal is trivalent and the ligand to metal molar ratio is about 3:1.

29. A composition comprising an admixture of electrically neutral amino Acid Chelates free of interfering ions and a stabilizing amount of calcium sulfate.

30. A composition as in claim 29, wherein the admixture is a free flowing dry particulate blend.

* * * * *